(12) United States Patent
Schütze (10) Patent No.: US 6,930,764 B2
(45) Date of Patent: Aug. 16, 2005

(54) LASER MICRODISSECTION SYSTEM (75) Inventor: Karin Schütze, Tutzing (DE)

(73) Assignee: P.A.L.M. Microlaser Technologies AG (DE)

( * ) Notice: Subject to any disclaimer, the term of this patent is extended or adjusted under 35 U.S.C. 154(b) by 0 days.

(21) Appl. No.: 10/491,927
(22) PCT Filed: Oct. 2, 2002
(86) PCT No.: PCT/EP02/11073
§ 371 (c)(1),
(2), (4) Date: Apr. 6, 2004
(87) PCT Pub. No.: WO03/036266
PCT Pub. Date: May 1, 2003

(65) Prior Publication Data
US 2004/0252291 A1 Dec. 16, 2004

(30) Foreign Application Priority Data
Oct. 24, 2001 (DE) .......................................... 101 52 404

(51) Int. Cl.[7] .................................................. G01N 1/00
(52) U.S. Cl. ........................................................ 356/36
(58) Field of Search ..................... 356/36–38, 402–425; 435/40.5, 174, 40.51, 7.1, 288.3, 6, 288.4, 7.2, 91.1, 455, 172.1, 375

(56) References Cited

U.S. PATENT DOCUMENTS 4,907,158 A  3/1990 Kettler ................... 364/413.01
5,998,129 A * 12/1999 Schutze et al. ................. 435/4
6,690,470 B1 * 2/2004 Baer et al. .................. 356/417
6,720,191 B1 * 4/2004 Goldstein et al. ........... 436/174
2001/0001574 A1  5/2001 Baer et al. ................... 356/244

FOREIGN PATENT DOCUMENTS

DE  37 18 066 A1  12/1988
DE  3836716 A1  5/1990
DE  100 15 157 A1  10/2001
EP  0 539 888 A1  5/1993
WO  WO 01/73398 A1  10/2001

OTHER PUBLICATIONS

English translation of the International Preliminary Examination Report for International Patent No. PCT/EP202/011 073 dated Jun. 24, 2003.

* cited by examiner

Primary Examiner—Tu T. Nguyen
(74) Attorney, Agent, or Firm—Peter F. Corless; Christine C. O'Day; Edwards & Angell, LLP

(57) ABSTRACT

A laser micro-dissection system, which is provided with a laser beam, in particular for the processing of biological material located on a carrier, comprises a laser, a microscope with a camera for the production of a microscope image or video image of the biological material located on the carrier and display screen for the display of the recorded video image, With the aid of suitable input means, a desired biological object to be processed with the laser beam, in the video images displayed on the screen, is selected and allocated to a corresponding object group. The control of the laser micro-dissection system, which can be realised in the form of a computer, automatically produces a list, in which on the one hand the individually selected objects and, on the other, a comprehensive representation of the object groups is contained.

24 Claims, 2 Drawing Sheets

| | | A | B | C | D | E |
|---|---|---|---|---|---|---|
| ☐ | ■ | 1 | Line | 7640 | | |
| ☐ | ■ | 2 | Line | 7350 | | |
| ☐ | ● | 3 | Line | 6800 | | |
| ☐ | ● | 4 | Line | 4245 | | |
| ☐ | ▲ | 5 | Line | 5111 | | |
| ☐ | ▲ | 6 | Line | 6450 | | |
| ☐ | ▲ | 7 | Line | 6240 | | |
| ☐ | ✳ | 8 | Line | 7440 | | |

17 — 18

19 ☑   20 OK   21 Cancel   22 Export

24 Delete ALL   25 Renumber   23 Save

26 Goto   27 Change   28 Delete

| | F | G |
|---|---|---|
| ■ | 2 | 14930 |
| ● | 2 | 11045 |
| ▲ | 3 | 17801 |
| ✳ | 1 | 7440 |
| Σ | 8 | 51276 |

29

30 ⊕→

31 [1] X

32 RoboLPC ▼

Fig. 3

LASER MICRODISSECTION SYSTEM

BACKGROUND OF THE INVENTION

The present invention relates to a laser micro-dissection system for the processing of a biological or non-biological mass, in particular a laser micro-dissection system for the processing, separation, and/or obtaining of microscopically small biological and/or non-biological objects of a biological or non-biological mass.

A conventional laser micro-dissection system of this kind from the Applicants is known from WO 97/29355 A or WO 01/73398 A. With the laser micro-dissection system described in these printed specifications, individual biological or non-biological objects, which are arranged on a planar carrier, can be selected with the assistance of a computer and processed with a laser beam. In this situation, a selected object can be separated from the surrounding mass, for example with the aid of a laser beam and with the assistance of a computer, in order for the selected object to be prepared free of the surrounding mass. The freely prepared object can then be catapulted by means of a laser-induced conveying process with the aid of a laser shot, which is directed onto the freely-prepared object, from the carrier to a catchment device. As a carrier, use can be made, for example, of a polymer film.

The method described previously allows for the separation, sorting, and obtaining of both biological as well as non-biological objects. Within the scope of the present patent application the term "biological objects" is understood to mean in particular living or fixed biological cells or cell constituents, which are constituent parts of a fluid or solid biological material, such as a piece of cell tissue, a smear, or a cell culture, etc. With the aid of the method described previously, the objects selected in each case are loaded specifically with a selected substance by means of contact-free laser microinjection, and the successfully injected biological objects are then sorted out. The biological objects may be located next to one another on a fixed planar carrier, whereby the process of separation can be carried out within a short time and free of contact. The survival capability and morphology of the biological objects is ensured; i.e. the biological objects are not damaged or impaired by the micro-injection procedure and by the separation and catapulting process.

In principle, the laser-induced conveying process explained previously, i.e. the catapulting out of objects previously selected individually from the surrounding mass in each case, can be carried out even without previous free preparation of the object selected in each case, if the laser energy and/or the laser focus at the moment of setting the separate laser shot is or are selected in such a way that the resulting impulse force of this laser shot is sufficient for releasing the corresponding object from the surrounding mass and for the conveying process to the catchment device.

Because the method described previously can be carried out manually with the desired degree of precision only with a relatively high degree of effort, the laser micro-dissection systems from the patent specifications referred to previously are designed to be computer-assisted, i.e. the cutting out and/or catapulting of a selected object is carried out with computer assistance, so that the laser light source which generates the laser beam which serves for the cutting and/or catapulting is actuated automatically, and the relative movement between the laser beam and the carrier with the biological or non-biological objects, required for the cutting and/or catapulting, is automatically induced and controlled. In particular, a computer-assisted selection or marking of the desired objects located on the carrier is possible, so that these can subsequently be processed automatically with the laser micro-dissection system. For this purpose the laser micro-dissection system comprises a display screen or monitor, on which a video image of the material located on the carrier, recorded by a digital camera, is displayed. The user can draw on the display screen or the video image, for example with the aid of appropriate graphic tools, a desired cutting curve, which is then followed automatically by the laser beam with computer assistance, in order to cut out the object selected in this way. In a similar manner, a desired object can also be marked on the display screen or video image in order for it to be catapulted out, whereby the separate laser pulse or laser shot is then imposed at the desired location.

Although with the known laser micro-dissection systems explained previously computer-assisted and automated processing of the material situated on the carrier is in principle already provided, nevertheless the processing of a number of biological objects, which in particular may be of different kinds, is relatively elaborate, since the objects may either be processed individually or in their entirety.

BRIEF SUMMARY OF THE INVENTION

The object of the present invention is therefore to provide a laser micro-dissection system of the type described previously with improved user friendliness and functional versatility.

This object is achieved according to the invention by a laser micro-dissection system with the features of claim 1. The subclaims relate in each case to preferred and advantageous embodiments of the present invention.

The present invention is described hereinafter on the basis of the cutting and/or catapulting of biological objects. The invention can also be applied to non-biological objects, however (inanimate material), which may be, for example, microscopically small objects made of glass, silica, plastic, etc., or artificially-manufactured vesicles etc. in a biological mass. The present invention can likewise be applied to non-biological masses or materials, e.g. polymer masses or the like, from which microscopically small objects can be released with the aid of the laser micro-dissection system.

The laser micro-dissection system according to the invention comprises a laser light source for the generation of a laser beam, which is to be directed onto the material to be processed and is located on an appropriate carrier. In addition, an image recording device, such as a CCD camera, is provided for, which generates a video or reproduction image of the material located on the carrier, and displays it on a display device, such as a screen of the laser microdissection system. This image is superimposed with a user interface of the laser micro-dissection system, in order in each case to be able to select the objects to be processed with the laser beam and allocate them to the object groups accordingly. The laser micro-dissection system comprises control means for the evaluation of the user selection carried out in this way, and for the production of a list in which the selected objects are contained, with an indication or designation of the object group allocated in each case, in such a way that, by orientation to the object group designation, a further selection of the objects and/or an object groupspecific selection is possible for subsequent processing with the laser beam. These control means are implemented in particular in a personal computer or the computer of the laser micro-dissection system.

A number of different marking types are available to the user for the selection and allocation of the desired objects to be processed with the laser beam, so that the user can, on the one hand, detect the desired object in each case on the display device with the assistance of a computer, for example by the appropriate selection of the marking, and, on the other, simultaneously allocate it to the corresponding object group, whereby another marking is assigned to each object group. Thus, for example, different colours can be offered to the user for the marking of the desired objects, whereby the user can, for example, by means of appropriate graphic aids, draw a cutting line on the display device for a biological object which is to be cut out, in the desired colour. In this way it is possible, for example, for healthy cells to be marked on the display device in a first colour, and tumour cells to be marked in a second colour, whereby in the list prepared by the control means the individual objects are sorted and compiled according to colour. By selecting an object group (which is displayed by the control means on the display device preferably with the corresponding colour) it is then possible for all the objects belonging to this object group to be processed automatically, i.e. computer-assisted, whereby the corresponding objects are approached one after another and, for example, cut out and/or catapulted out with the aid of the laser beam. Obviously, instead of marking by means of different colours, any other type of marking with the power of differentiation is also possible. Thus, for example, a cutting line drawn on the video image around a desired object can have superimposed on it an unambiguous identifier which identifies the desired object group in each case.

The selection of the objects compiled in an object group can, as already described, also be carried out manually by the operator as well as automatically and with computer assistance by digital image processing/image evaluation, whereby in the latter case a differentiation may be made in an inherently known manner by means of fluorescence evaluation or the like between healthy cells or tumour cells etc., and an allocation may be made automatically to a corresponding object group. The term "selection means" used herein therefore comprises both a manual selection as well as an automatic software-controlled or computer-controlled selection of the desired objects.

By means of the method described previously it is possible for the previously selected and marked objects to be processed with the laser beam in a group-specific manner. In other words, for example, in the first instance all the objects allocated to a first object group can be processed with the laser beam, while thereafter all the objects allocated to a second object group can then be processed. This enables all the objects of the first object group to be collected in a first catchment container and all the objects of the second object group to be collected in a second catchment container after the performance of the cutting and/or catapulting procedure. The objects in the first group, as has already been mentioned, may, for example, be tumour cells, while the objects of the second group may, for example, be healthy cells. The separation of the desired objects is in this way clearly simplified and speeded up.

Advantageously, as a consequence of the group-specific laser processing, a different type of laser processing can be selected and applied for each object group. To do this, a plurality of different laser functions are provided by the laser micro-dissection system, whereby, in particular, the number of repetitions of the predetermined laser processing can also be selected separately for each object group.

The list produced by the control means of the laser micro-dissection system, in which the objects selected previously by the user are compiled group by group, preferably comprises for each group an indication of the number of objects contained in it, as well as the total surface area of the objects contained in it. To do this, the laser micro-dissection system is equipped with an automatic surface area calculation function, which makes it possible, after the drawing of a cutting line around a desired object, for the area of the object thus selected and enclosed by this cutting line to be calculated. In this way, important additional information is provided to the user with regard to the objects being processed, classified according to the individual object groups.

In addition to the list section explained previously, a list section is preferably also produced by the control means which may contain information about each object to be processed individually, about the particular object type in each case, about the individual object surface area in each case, and/or about the object group to which allocation has been made. In respect of the object type, for example, a differentiation can be made as to whether this is an object defined by a cutting line or only an object defined by its catapult point, etc. Within this list section each individual object, or any desired selection of the objects represented, can be marked in order for the correspondingly marked objects to be able then to be processed jointly with the desired laser function.

The list created by the control means may optionally also exhibit only the list section first referred to, in which the selected objects are compiled object group by object group, or only the list section referred to in the second case, in which the individually selected objects are contained. It is important, however, that in each case an object group indication is provided, in order to allow for a further selection on the basis of the object group indication.

The list produced by the control means and the object information contained in it can be stored in a suitable storage medium or in the working memory of the laser micro-dissection system. In this situation it is advantageous for a reference position on the corresponding carrier to be determined for the selected objects, to which the individual object positions of the selected objects relate, so that, when later processing the corresponding carrier and when loading the stored object information, taking the previously determined reference position as a starting point, simple approach and finding of the stored object positions relative to this is possible.

The compilation of the selected object in object groups also makes it possible, after the laser processing of the objects of a specific object group, for the positions of the corresponding objects on the object carrier to be approached again one after another, in order for a check to be made that the cutting out or catapulting of the corresponding objects has been carried out properly, and this can be done both by the operator visually, by checking the cutting or catapulting lines on the display screen as well as automatically by computer-assisted evaluation of the cutting or catapulting lines by means of digital image processing or image analysis.

A pulsed UV laser is preferably used as a laser source for the laser micro-dissection system,. A glass object carrier can be used as a carrier, which may preferably be coated with a carrier film, consisting of a UV-absorbing polymer film with a thickness of, for example, 5 $\mu$m and 15 $\mu$m, whereby the absorption behaviour of the carrier film is adapted to the wavelength of the UV laser, and therefore preferably has an absorption maximum in the vicinity of the laser wavelength.

Likewise, carrier films or carrier membranes or even teflon membranes in the form of what are known as Petri dishes etc., tensioned on frames, may be used as carriers. A catchment substrate can be used as a catchment device for catching and taking up objects released from the material being processed, which catchment substrate may be designed in the form of a film or plate, or even in the form of a pot-shaped container. In particular, microcentrifuge containers are recommended as catchment devices, such as are used in molecular biology, or the caps of these, whereby in particular several catchment containers of this kind may be arranged next to one another, in order for different objects to be conveyed one after another in different catchment containers. Likewise, the use of a microtiter plate as a catchment device is possible, with a number of wells, so that a plurality of objects may be caught one after another by different wells. The catchment device can be provided with an adhesive layer, so that objects which are released can be fixed by means of the adhesive layer. An adjustment device, capable of computer-assisted control, is preferably provided for the carrier and/or the catchment device, in order to allow for automatic positioning of these units.

The function of the control means according to the invention, as explained previously, is implemented, in particular in terms of software, in the form of a suitable control program for the laser micro-dissection system. The present invention therefore relates not only to the laser micro-dissection system as such, but also to the design of the corresponding control program or the computer-readable storage medium, which stores this control program.

BRIEF DESCRIPTION OF THE DRAWINGS

The present invention is explained hereinafter in greater detail by making reference to the appended drawings and on the basis of preferred embodiments.

DETAILED DESCRIPTION OF THE INVENTION

Figure 1:
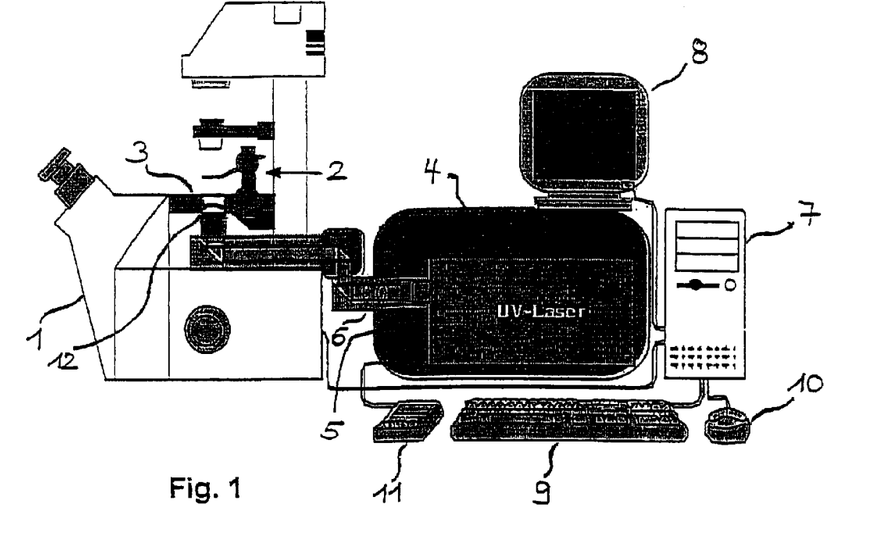
FIG. 1 shows the structure of a laser micro-dissection system in accordance with a preferred embodiment of the present invention.

The laser micro-dissection system shown in FIG. 1 comprises a laser device 4, in which a laser light source is located for the production of a laser beam. In addition, a lens 6 is located in the laser device 4, which is required in order to couple the laser beam into a microscope 1 and for the laser focus to be adjusted in the object plane to the optical focus of the microscope 1. In the present case, for example, this involves a pulsed UV nitrogen laser with a wavelength of 337 nm, a pulse energy of 270 $\mu$J, a pulse duration of 3 ms, and a pulse frequency of 1–30 pulses/second.

For the precise adjustment of the laser energy, a quartz filter 5 is arranged perpendicular to the path of the laser beam, which can be adjusted manually by means of a control panel (not shown) to the corresponding setting of the laser energy, or can also be adjusted automatically. In addition to the adjustment setting of the laser energy, the laser focus can also be adjusted independently of the microscope focus; i.e. the focal point of the laser can be displaced in the z direction relative to the object plane of the microscope 1, whereby for this purpose the lenses 6 shown in FIG. 1 can be moved by means of a stepping motor. This adjustment can also be carried out manually as well as automatically.

The laser beam is coupled into the microscope 1 via several coated beam splitters, and deflected to a lens 12. The diameter of the laser beam which impinges on the object plane is significantly dependent on the numerical aperture of the lens 12. A lens with a relatively high numerical aperture allows for laser beam diameters of less than 1 $\mu$m to be achieved. In addition to this, attention must be paid to the fact that the lens 12 used in each case exhibits a high permeability for the individual laser wavelength, in order to minimise energy losses.

The laser beam emitted via the lens 12 finally impinges onto a motorised and computer-controlled microscope table or carrier table 3, on which a carrier is arranged with a biological material which is to be processed. Located above the carrier table 3 is a manipulator 2, which is manually actuatable or preferably likewise motorised and computer-controlled. The components 2 and 3 enable exact object positioning with high precision, as well as automatic performance of u-manipulation procedures.

The motorised carrier table 3 can be moved along two linear axes (x/y direction). For example, a needle or micropipette for micro-injection can be situated at the motorised manipulator 2. Within the framework of the present invention, however, it is assumed that a catchment device is located at the manipulator 2, in order to catch the biological objects catapulted away from the carrier. The motorised manipulator 2 can be moved in both the x/y direction as well as in the z direction.

The microscope 1 can be a microscope of any desired design. In particular, both the use of an inverse as well as an upright microscope or a laser microscope is conceivable. The laser micro-dissection system represented in FIG. 1 is an inverse arrangement, in which the laser beam impinges onto the carrier from below, in order to catapult the biological objects located on it upwards to the catchment device. With an upright arrangement, by contrast, the laser beam impinges onto the carrier from above, so that objects released from the biological material are catapulted or fall downwards, as a function of the laser energy, onto the catchment device located beneath the carrier.

The microscope 1 is equipped with a video camera, in particular a CCD ("Charge Coupled Device") video camera, which records the area of the carrier 3 above the lens 12.

The video signal from this video camera is conducted to a conventional commercial computer ("personal computer") and there processed so that a corresponding video image van be represented in real time on the display screen or monitor 8 of the computer 7. Likewise, the storage of individual video images on a suitable storage medium of the computer 7 is possible. In addition to this, it is also possible for an analogue or digital video recorder to be coupled to the computer 7 for recording the video images provided by the video camera.

As described in greater detail hereinafter, a variety of different functions are implemented on the computer 7 or by the software running on it, which allow for both a computer-assisted, i.e. automatic, actuation of the laser device 4 as well as of the microscope 1, so that, for example, the laser can be automatically activated and the manipulator 2 and carrier table 3 respectively can be moved. Likewise, these computer-assisted functions allow for a particularly user-friendly selection and processing of desired biological objects from the biological material located on the carrier. To adjust and select these functions, conventional input means are provided, such as a keyboard 9 or a computer mouse 10. In addition, a foot switch 11 is assigned to the laser device 4, by the activation of which the laser can be activated manually.

The functions provided by the laser micro-dissection system shown in FIG. 1 are described hereinafter in greater detail.

Figure 2:
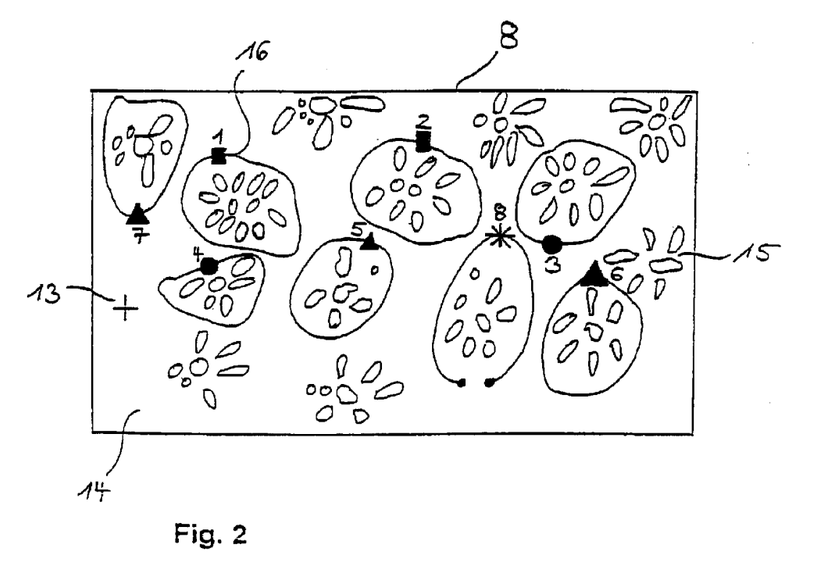
FIG. 2 shows the representation of an example of a display screen image of the laser micro-dissection system shown in FIG. 1, for the selection and marking of desired biological objects.

After the computer 7 has been switched on, the microscope image which is being taken at that particular moment by the video camera is displayed on the screen 8, as shown, for example, in FIG. 2. The laser target point 13 is represented in FIG. 2 by a cross. In addition to this microscope image, the screen also displays adjustment and setting possibilities which can be realised by software for adjusting the laser energy, the laser focus, the laser function, the enlargement of the lens 12 used, for storing the microscope image shown, etc, or possibilities for calling up other menu windows, which will not be dealt with at this juncture in any greater detail. The control program is controlled essentially by means of the computer mouse 10 shown in FIG. 1, whereby, however, the essential functions can also be called up by corresponding key combinations of the keyboard 9.

Essentially, a distinction can be drawn between two different operating modes.

In what is referred to as the cursor mode, menus can be opened with the aid of the mouse 10, corresponding menu functions selected, and what are referred to as buttons can be clicked on. In the move mode, by contrast, movements of the mouse 10 are converted directly into corresponding adjustment signals and therefore corresponding mechanical movements of the carrier table 3 or the manipulator 2. A status window can be displayed beneath the microscope image, which shows, inter alia, whether the control system is currently in the cursor mode or the move mode. This status window can, in addition, display the X and Y coordinates which define the absolute position (in $\mu$m) of the microscope table or carrier table 3 related to a zero position.

In addition to the functions explained previously, as well as the microscope image what are referred to as graphic tools are displayed on the screen 8, with the aid of which freehand lines or predetermined figures can be drawn on the screen 8 or on the microscope image being displayed, for example rectangles, circles, straight lines or ellipses, so that the microscope image is shown on the screen 8 with these graphic elements superimposed on it. In addition, a colour palette can be displayed on the screen 8, so that for each element drawn the desired colour which appears on the screen 8 can be selected. In this situation, the colour which is selected in each case is stored as a standard default for all the elements of the element type selected at that particular moment. In this way it is possible for different biological objects from the biological material 14 located on the carrier 3, which is being displayed in the form of a video or microscope image on the screen 8, to be selected and marked by different colours.

With the example shown in FIG. 2, it is assumed that the user has, with the aid of the graphic tools explained previously, placed a freehand cutting line 16 in a first colour, which is indicated in FIG. 2 by a square, around two biological objects. In a second colour, which is indicated in FIG. 2 by a circle, two further objects have been marked with the aid of corresponding freehand cutting lines. Three further objects have been selected and marked in an analogous manner by a freehand cutting line in a third colour, which is indicated by a triangle. In a fourth colour, which is indicated by a star, a further freehand cutting line has been laid around a further biological object, whereby, however, in contrast to the freehand cutting lines referred to previously, this freehand cutting line is not entirely closed. The cutting lines shown in FIG. 2 serve not only for the marking and selection of the corresponding biological objects but also for the subsequent laser processing of the biological material 14 located on the carrier table 3, as well as specifying the automatic relative movement between the carrier table 3 and the laser beam of the laser device 4, in order to guide the laser beam along the cutting line specified in each case, and therefore to prepare the biological object selected in each case from the surrounding biological mass.

Within the framework of the present embodiment it is assumed that the different biological objects 15 are marked for the subsequent laser processing in different colours, whereby all the objects marked in one and the same colour form a corresponding object group. Obviously, however, apart from the use of different colours, another type of marking of the individual biological objects on the screen 8 is also possible. Thus, for example, as shown in FIG. 2, for each cutting line another type of graphic representation can be selected (in FIG. 2 with a rectangle, circle, triangle, or star). This is only significant with regard to the fact that the marking is in each case selected in such a way that the clearest possible distinction between the individual groups is possible in which the biological objects are compiled with the same marking.

In the example shown in FIG. 2, the graphics tools explained previously are adjusted in such a way that each biological object marked or selected by a freehand cutting line 16 is provided with a serial number, which is also displayed on the screen 8. The biological objects with the numbers "1" and "2", the biological objects with the numbers "3" and "4", the biological objects with the numbers "5"–"7", and the biological object with the number "8" therefore form one object group in each case. The display of these numbers on the screen 8 may optionally also be deactivated. In addition to this, the software of the laser micro-dissection system also comprises a function with which the distance can be measured between two points selected on the microscope image. Thus, for example, a start point can be selected on the microscope image, whereby the measurement of the distance to this start point is carried out automatically during the movement of the mouse 10 when a corresponding mouse key of the mouse 10 is held pressed down. Likewise, the software may exhibit a function for the automatic calculation of the surface content of a biological object selected and/or marked in the manner described previously, which is delimited by a cutting line 16 drawn previously. The surface content of the individual biological object in each case is then represented, for example, in $\mu$m$^2$ on the screen 8 of the laser micro-dissection system. As a further function, the graphics tools of the laser micro-dissection system can also exhibit an "eraser" function, in order to delete graphic elements drawn previously on the screen 8. Likewise, by means of a corresponding function, a text commentary which may be desired can be inserted at any desired point of the video image represented on the screen 8.

The marking or selecting described previously of the desired biological object 15 serves to select the biological objects desired for subsequent laser treatment, i.e. those biological objects are determined which it is intended should be later automatically freely prepared and/or catapulted to the catchment device. For the biological objects selected in this manner, an entry is generated in each case in a list which is likewise represented on the screen 8. The structure of this list is explained hereinafter in greater detail, by making reference to FIG. 3.

Figure 3:
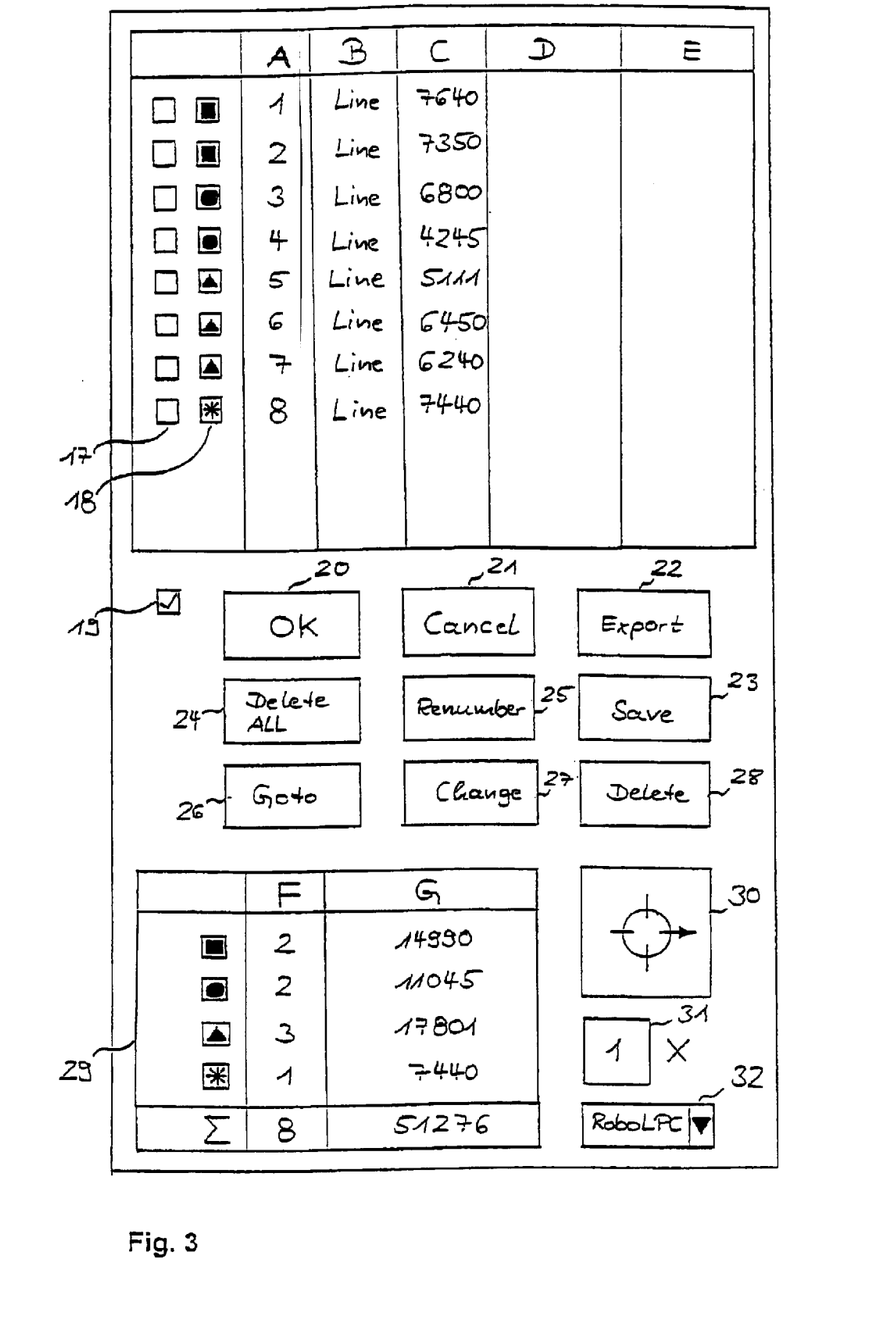
FIG. 3 shows by way of example a display screen representation of the laser micro-dissection system shown in FIG. 1 with a list in which are contained biological objects perviously selected and marked by a user.

In an upper list section in FIG. 3, an entry or an element is provided for each previously selected object. In a column A the individually selected or marked object is provided with a serial number in the sequence of its marking by analogy with FIG. 2. In a column B an indication is provided for each element as to what type is involved, whereby in particular a distinction is made between a "line" type for a cutting line and a "dot" type for an individual catapulting point, which can likewise be determined with the specified graphics tools on the video image. With the example shown in FIG. 3, all the elements are previously-drawn lines. In addition, in a column C, the surface area (for preference in $\mu m^2$) is indicated for each selected biological object as enclosed by the corresponding cutting line. In addition, in a column D a corresponding commentary may be optionally inserted for each entry.

As can be seen from FIG. 3, in a further column 18 the marking or colour is indicated which has been selected for each element or for each object respectively during the selection of the object in each case.

The list is continually updated. In other words, during the marking of further biological objects required by the user on the screen 8, a new entry is automatically generated in the list for each additionally marked biological object.

In a lower list section 29 a compilation representation is shown in which the objects are sorted and grouped according to object groups or markings/colours. In this situation, for each marking/colour the number of objects contained in each case is indicated in a column F, and in a column G the total surface area of the objects allocated to this object group. A concluding line of this list section 29 provides an indication of the total number of the objects from all the object groups, i.e. the total number of all marked objects and their total surface area.

With the example represented in FIG. 3, a selection field 19 is activated, whereby with this activation only list entries of the "line" type are represented. Entries of the "dot" type or also text entries etc., however, are not represented on the activation of the selection field 19.

By clicking on a button 20, the list which is represented can be stored and closed. By clicking on a button 21, by contrast, the list can be closed without storing, and is therefore discarded. By clicking on a button 22, all the elements of the list and its properties (e.g. marking/colour, number or type, etc.) and the compiled values can be exported into a file.

A button 23 enables the storage of all the elements of the list represented in a file, whereby in particular, for each element or for each biological object respectively, the position in relation to a previously selected reference position of the biological material in each case can also be stored. Before storing, therefore, this reference position of the carrier, and of the biological material located on it respectively, must be determined with computer assistance. This reference position is necessary in order to ensure, in the event of a renewed use of a previously examined biological material, that the biological objects selected and marked there can be correctly approached and positioned. In this situation, a different reference position can be determined for each object carrier and for each specimen respectively.

When the object carrier is positioned, therefore, the desired biological objects are then moved in relation to the previously determined reference position, i.e. the position data stored for each element or for each biological object selected is relative position data, which is related to the previously determined reference position. By means of a corresponding software function, when determining the reference position on the microscope image shown it is possible for the user to mark this position with the laser in the biological material, so that the reference position can later be found easily.

The activation of a button 24 enables the deletion of all the elements on the list represented, while a button 28 only permits the deletion of one or more selected elements from the list. By clicking on a button 25, the elements on the list which then remain can be renumbered.

With the aid of a button 26, each individual biological object can be approached in such a manner that it appears centered on the screen 8. For the centered representation of the object number "5" only the corresponding line in the upper line section of FIG. 3 need be marked with the mouse 10, and the button 26 then activated.

Each individual element and each individual biological object respectively can be processed separately with the laser beam. If, for example, it is intended that the biological object No. "5" is to be processed, only the corresponding entry in the upper list section is marked with the mouse, and a laser start button 30 then activated.

With computer assistance the laser beam is then positioned by an appropriate relative movement between the laser beam and the carrier table 3 on the desired cutting line, drawn in beforehand according to FIG. 2, of the biological object in each case, and is moved along the cutting line drawn in previously, in order to prepare the biological object freely. In an analogous manner, several of the selected biological objects selected can also be marked and then processed by the activation of the laser start button 30 one after another.

It is particular advantageous, however, if a corresponding selection can also be effected in the lower list section 29 of single or several object groups, so that, after the subsequent activation of the laser start button 30, only the selected object group or the biological objects belonging to the selected object groups are processed.

If, for example, it is intended that tumour cells are to be placed in a catchment container and healthy cells in a further catchment container, it is recommended that, during the movement of the microscope image represented on the screen 3 according to FIG. 2, the desired cells are to be marked in such a way that the cutting lines of the tumour cells are identified in a first colour and the cutting lines of the healthy cells are identified in a second colour. Thus, for example, it is assumed that for the tumour cells the colour blue is used for the marking, while for the healthy cells the colour yellow is used. In the lower list section 29, then, a line would appear with a compilation of the "blue" tumour cells and a line with the compilation of the "yellow" healthy cells. By marking the "blue" line ("highlighting"), the corresponding positioning of the catchment container by means of the laser beam, and the subsequent activation of the laser start button 30, all the "blue" tumour cells are then processed with the laser beam and, depending on the laser function which has been set in selection field 32, are catapulted into the catchment container. The "yellow" line can then be marked with the mouse 10, a new catchment container positioned by means of the laser beam, and the laser start button 30 activated again, so that all the "yellow" healthy cells are caught in the second catchment container.

In this respect, the laser micro-dissection system is designed advantageously in such a way that the different catchment containers for the individual object groups and/or objects are automatically positioned and therefore moved into the catchment position; i.e. before the processing of the objects of a selected object group, in each case a corresponding catchment container is moved into the catchment position, so that the objects of one and the same object group are in each case collected in one and the same catchment container, which makes storage and subsequent analysis of these objects easier.

In the upper list section, in addition to column 18, a further column 17 is provided, in which the processing status is displayed for each element or for each biological object. As soon as a biological object has been processed with the laser beam after the activation of the laser start button 30, the "checkbox" which corresponds to this biological object or this list entry is marked.

For each activation of the laser start button 30, the number of repetitions of the laser treatment can be input by inputting a corresponding value into a further selection window 31. In the example shown in FIG. 3, there is only a simple operation of the laser function which has been set in accordance with the selection window 32.

As has already been explained briefly previously, it is possible, with the aid of the selection window 32 for a specific laser function from among several which are predetermined to be selected for each laser processing. In the laser function "RoboLPC" which has been preset according to FIG. 3, when the laser start button 30 is activated the cutting line drawn previously of the individual biological object in each case is automatically run through as far as a predetermined residual slat or blade, and a separate laser shot is then directed onto the centre of this slat or blade, in order for the desired biological object to be catapulted out of the surrounding biological mass into the catchment container. If, during the prior drawing of the cutting line, as with the biological object shown in FIG. 2 with the number "8", the cutting line is left further open such as would correspond to the width of this slat or blade which has been preset in the system, then this over-dimensioned gap will automatically be reduced by a straight line to the predetermined width of the slat.

A further laser function "LPC" can be provided, for example for setting separate catapulting laser shots, i.e. a laser shot is set at the desired point without previous free preparation, in order to catapult the corresponding biological object out. With specific preparations, such as, for example, cyto-centrifuged cells, this separately set laser shot may already be sufficient to cause the catapulting. A further laser function, "Cut", can be provided in order to cut only along the previously-drawn cutting line, without a subsequent catapulting laser shot being set. The laser shot can then be set separately at a desired position on the freely prepared biological object with the aid of the laser function explained previously. With this pure cutting function, too, the biological object in each case is preferably not freely prepared in its entirety, but a narrow residual slat or blade of predetermined width is left standing. A further laser function, "CloseCut", may correspond to the cutting function explained previously, whereby, however, the previously drawn cutting line is moved over in its entirety by the laser beam, in order for the biological object in each case to be freely prepared in full. If the cutting line is not entirely closed by the user, the start and end points of the cutting line will be connected by a straight line by the laser micro-dissection system, in order to obtain a closed cutting line. A further laser function, "AutoLPC", which can be set by means of the selection window 32, can be provided for the carrying away of a surface marked beforehand on the microscope image, or a previously-marked biological object respectively. When this laser function is selected, the area inside the previously drawn line is carried away by a number of laser shots placed one after another, and catapulted into the corresponding catchment container. The number of laser shots per surface unit can in this case be set by a corresponding menu of the laser micro-dissection system. Finally, a further laser function, "CloseCut & AutoLPC", makes provision for a combination of the two laser functions explained previously; i.e. the desired biological object is first separated from the surrounding biological mass with the aid of a completely closed cutting line, and then carried away by a number of laser shots set one after another, and conveyed into the catchment container. This procedure is especially applicable if the user wishes to exclude any risk of contamination of the biological material which is to be carried away due to adjacent biological material.

For each laser processing procedure, i.e. for each activation of the laser start button 30, the laser function can therefore be adjusted and set by means of the selection window 32 and the number of repetitions of this laser function by means of the selection window 31. On the other hand, for each activation of the laser start button 30, by corresponding marking of the desired elements or objects or object groups, a selection can be made in the list shown as to whether the corresponding procedure should extend to individual objects or to whole object groups.

As has already been explained previously, in the column 17 the corresponding "checkbox" is set for each object processed, as soon as the processing for this object has been concluded. At the same time, in column E the number of cutting or catapulting procedures carried out for the corresponding object is specified and displayed.

The arrangement explained previously of the laser micro-dissection system makes it possible, for example, for the biological objects grouped in different object groups to be processed with the laser in different ways. Thus, for example, for the objects of a first object group only the laser cutting function is set, while for the objects of a second object group the "RoboLPC" laser function is provided for, as predetermined in FIG. 3. In this way the greatest possible degree of flexibility is achieved.

What is claimed is:

1. A laser micro-dissection system for processing a material located on a carrier, comprising
 a laser light source for generating a laser beam to be directed onto the material to be processed, in order to process the material with the laser beam,
 an image recording device for producing of an image of at least one section of the material located on the carrier,
 a display device for representing the image produced by the image recording device,
 selection means for selecting objects to be processed with the laser beam from the material located on the carrier and for allocating of the object selected in each case to a corresponding object group, and
 control means for evaluating the selection carried out with the aid of the selection means of the objects to be processed and for producing a list in which the selected objects or the object groups are contained, with a designation of the corresponding object group in each case, whereby, by means of the selection means, any object group in the list can be selected, and the control means are designed in such a way that they arrange for the processing of the objects allocated to the selected object group in a group-specific manner with the laser beam.

2. A laser micro-dissection system according to claim 1, wherein the object to be processed can be selected by the corresponding marking of the object on the image represented by the display device of the material located on the carrier, and in that the control means are designed in such a way that they provide different types of marking, whereby each type of marking is allocated to an object group so that all the objects marked and selected with a specific kind of marking form a corresponding object group.

3. A laser micro-dissection system according to claim 2, wherein the control means are designed in such a way that, in the list section of the list for each object group, the marking used in the selection of the corresponding objects (15) is indicated.

4. A laser micro-dissection system according to claim 1, wherein the control means are designed in such a way that they provide the list with a list section, in which the selected objects are compiled in the corresponding object groups.

5. A laser micro-dissection system according to claim 4, wherein the list with the list section is represented on the display device by the control means, and in that, by means of the selection means, the object group can be selected in the list section and the control means are designed in such a way that they arrange for a processing of the objects allocated to the selected object group with the laser beam.

6. A laser micro-dissection system according to claim 4, wherein the control means are designed in such a way that, contained in the list, is the number of the objects allocated to this object group, and for each object group.

7. A laser micro-dissection system according to claim 4, wherein the control means comprise a surface area calculation function for calculating the surface area of an object selected via the selection means, and in that the control means are designed in such a way that, contained in the list section of the list, is the total surface area of all the objects allocated to the corresponding object group, and for each object group.

8. A laser micro-dissection system according to claim 1, wherein the control means are designed in such a way that they produce the list with a list entry with object information regarding the objects which are selected via the selection means and which are to be processed with the laser beam.

9. A laser micro-dissection system according to claim 8, wherein characterised is the object to be processed that can be selected by marking the corresponding object by means of the selection means on the image represented by the display device of the material located on the carrier, in that the control means provide different types of marking for marking the objects to be processed, and in that the control means are designed in such a way that each list entry of an object selected and to be processed with the laser beam contains a representation of the type of marking used for marking the individual object in each case.

10. A laser micro-dissection system according to claim 8, wherein the control means comprise a surface area calculation function for the calculation of the surface area of an object selected by the selection means and which be processed with the laser beam, and in that the control means are designed in such a way that they produce the list entries with object information indicating the object surface in each case for the selected objects.

11. A laser micro-dissection system according to claim 8, wherein the control means are designed in such a way that each list entry contains an indication as to whether the corresponding object has already been processed with the laser beam or not.

12. A laser micro-dissection system according to claim 8, wherein the control means are designed in such a way that the list entries from the list produced by the control means contain an indication of the type of the corresponding object.

13. A laser micro-dissection system according to claim 8, wherein the control means display the list on the display device, in that by means of the selection means any desired list entry can be selected from the list displayed on the display device, and in that the control means are designed in such a way that they allow for processing by the laser beam of the objects corresponding to the selected list entries.

14. A laser micro-dissection system according to claim 1, wherein the control means, in the event of the presence of a corresponding selection by means of the selection means, arrange for processing with the laser beam of the objects or object groups selected in the list by means of the selection means, in accordance with a laser function which can be selected via the selection means.

15. A laser micro-dissection system according to claim 14, wherein by way of the selection means the laser function desired in each case can be selected from a group of predetermined laser functions, whereby the group of laser functions comprises at least one first laser function for cutting with the laser beam along a cutting line specified by the selection means and a second laser function for setting a laser shot at a position specified by the selection means on the material located on the carrier.

16. A laser micro-dissection system according to claim 14, wherein by way of the selection means the number of repetitions of the processing of the objects or object groups selected by the selection means can be adjusted and set with the laser beam.

17. A laser micro-dissection system according to claim 1, wherein the control means comprise a surface area calculation function for calculating the surface area of the object selected by the selection means, and in that the control means are designed in such a way that they produce the list with an indication of the total number of all the objects selected by the selection means, and with an indication of the total surface area of the objects selected by the selection means.

18. A laser micro-dissection system according to claim 1, wherein by means of the selection means the object to be processed with the laser beam is selected by the corresponding marking of the object to be processed in the image represented on the display device of the material located on the carrier, and in that the control means are designed in such a way that they provide different types of marking for the marking of the objects to be processed, and allocate all the objects marked by the selection means with the same type of marking to a corresponding object group, so that each object group comprises objects marked with one and the same type of marking.

19. A laser micro-dissection system according to claim 18, wherein the different types of marking are different marking colours, with which the objects to be processed are marked on the image represented on the display device of the material located on the carrier.

20. A laser micro-dissection system according to claim 1, wherein the list can be stored in storage means.

21. Laser micro-dissection system according to claim 20, wherein the control means comprise a function for the determination of a reference position on the material located on the carrier, and in that the control means are designed in such a way that, when the list is stored in the storage means, the positions of the selected objects in the material located on the carrier are stored in relation to the reference position.

22. A laser micro-dissection system according to claim 21, wherein the control means are designed in such a way that they comprise a function for the specific approach to a selected object contained in the list, whereby the control means are designed in such a way that they determine the position of the corresponding object in relation to the reference position, and, taking the reference position as a starting point, arrange for an adjustment of the carrier in such a way that the corresponding object of the material located on the carrier appears at a specific point in the image represented on the display device.

23. A computer-readable storage medium, in which a control program is stored for the computer-assisted control of a laser micro-dissection system for processing a material located on a carrier, whereby the laser micro-dissection system comprises:

a laser light source for producing a laser beam to be directed onto the material, in order for the material to be processed with the laser beam, an image recording device for producing an image of at least one section of the material located on the carrier, a display device for representing the image produced by the image recording device, and selection means for selecting objects, to be processed with the laser beam, from the material located on the carrier, and for allocating the object selected in each case to a corresponding object group, whereby the control program is arranged in such a way that, during operation in the computer-assisted controlled laser micro-dissection system, it assesses the selection of the objects to be processed with the aid of the selection means, produces a list which can be represented on the display device, in which the selected objects or the object groups are contained with a designation of the corresponding object group in each case, and, at the selection of any desired object group in the list by means of the selection means, processing of the objects allocated to the selected object group is arranged in a group-specific manner with the laser beam.

24. A computer-readable storage medium according to claim 23, wherein the control program is arranged in such a way that, when implemented in the computer-assisted controlled laser micro-dissection system, the function of the control means of the laser micro-dissection system is carried out for evaluating the selection carried out with the aid of the selection means of the object to be processed and for producing a list in which the selected objects or the object groups are contained, with a designation of the corresponding object group in each case, whereby, by means of the selection means, any object group in the list can be selected, and the control means are designed in such a way that they arrange for the processing of the objects allocated to the selected object group in a group-specific manner.

* * * * *